(12) United States Patent
Shimoda et al.

(10) Patent No.: US 8,268,919 B2
(45) Date of Patent: Sep. 18, 2012

(54) POLYMER FOR DETECTING FINGERPRINT, METHOD OF PRODUCING THE SAME, COMPOSITION FOR DETECTING FINGERPRINT AND METHOD OF DETECTING FINGERPRINT USING THE SAME

(75) Inventors: Osamu Shimoda, Hyogo (JP); Masahisa Takatsu, Hyogo (JP); Muneaki Kano, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 572 days.

(21) Appl. No.: 12/311,606

(22) PCT Filed: Sep. 28, 2007

(86) PCT No.: PCT/JP2007/069007
§ 371 (c)(1),
(2), (4) Date: May 8, 2009

(87) PCT Pub. No.: WO2008/044494
PCT Pub. Date: Apr. 17, 2008

(65) Prior Publication Data
US 2010/0047433 A1 Feb. 25, 2010

(30) Foreign Application Priority Data

Oct. 6, 2006 (JP) ................................. 2006-274958

(51) Int. Cl.
*C08G 65/26* (2006.01)
*C08F 2/00* (2006.01)
*A61B 5/103* (2006.01)
*A61B 5/117* (2006.01)

(52) U.S. Cl. ............................. 524/242; 526/208; 427/1
(58) Field of Classification Search ................ 542/242; 427/1, 145; 526/208
See application file for complete search history.

(56) References Cited

U.S. PATENT DOCUMENTS 4,364,876 A * 12/1982 Kimura et al. ................ 558/443
(Continued)

FOREIGN PATENT DOCUMENTS

JP      S60-22203       2/1985
(Continued)

OTHER PUBLICATIONS

Sodhi et al., "A fingerprint powder formulation involving yellow dye," *Research and Practice in Forensic Medicine*, vol. 47, Nov. 30, 2004, pp. 237 and 238.

*Primary Examiner* — Kelly M Gambetta
(74) *Attorney, Agent, or Firm* — Fitch, Even, Tabin & Flannery, LLP

(57) ABSTRACT

It is intended to provide a polymer for detecting a fingerprint, which can be easily handled in a scene of the fingerprint detection as a substitute for conventionally employed 2-cyanoacrylate (a monomer), and a composition for detecting a fingerprint. It is also intended to provide a method of detecting a fingerprint whereby a fingerprint can be detected at a high sensitivity regardless of the color or conditions of a specimen and wherein the specimen can be well restored. The present polymer and composition for detecting a fingerprint and method of detecting a fingerprint using the same make it possible to definitely detect a fingerprint by using fluorescence even from an almost white specimen such as a shopping bag or an aluminum foil from which a fingerprint can be hardly detected by the existing methods.

2 Claims, 1 Drawing Sheet

U.S. PATENT DOCUMENTS

| | | | |
|---|---|---|---|
| 4,477,607 A | | 10/1984 | Litke et al. |
| 4,504,408 A | * | 3/1985 | Morton .................... 252/301.16 |
| 4,719,119 A | | 1/1988 | Thompson et al. |
| 4,806,380 A | | 2/1989 | Sato et al. |
| 5,561,198 A | * | 10/1996 | Huver et al. .................. 525/379 |
| 6,127,189 A | * | 10/2000 | Joullie et al. .................. 436/111 |

FOREIGN PATENT DOCUMENTS

| | | | |
|---|---|---|---|
| JP | S60-502088 | | 12/1985 |
| JP | S61-288836 | | 12/1986 |
| JP | S62-473343 | | 3/1987 |
| JP | S63-161939 | | 7/1988 |
| JP | H11-99777 | | 4/1989 |
| JP | 02-268744 | * | 11/1990 |
| JP | H02-268744 | | 11/1990 |
| JP | H6-165771 | | 6/1994 |
| JP | H11-9575 | | 1/1999 |

* cited by examiner

POLYMER FOR DETECTING FINGERPRINT, METHOD OF PRODUCING THE SAME, COMPOSITION FOR DETECTING FINGERPRINT AND METHOD OF DETECTING FINGERPRINT USING THE SAME

CROSS-REFERENCE TO RELATED APPLICATIONS

This is a U.S. National Phase of International Application PCT/JP2007/069007, filed Sep. 28, 2007, and claims foreign priority under 35 U.S.C. §119 based on Japanese Application No. 2006-188034, filed Oct. 6, 2006, the entire disclosures of which applications are hereby incorporated herein by reference.

TECHNICAL FIELD

The present invention relates to a detection of fingerprint in the field of criminal identification technologies.

BACKGROUND ART

Detection of a latent fingerprint is an important means for criminal investigation, which will be evidence necessary for identification, arrest and charge of criminals. In most cases, the detection of fingerprint is conducted by the following method. A surface of a specimen to which fingerprint is attached or suspected to be attached is swept softly with a brush containing aluminum powder so that the aluminum powder sticks to the fingerprint, and then the powder is copied onto gelatin paper. However, when the specimen is a specific material including a metallic deadly weapon such as a handgun and a knife, a synthetic leather, and an adhesive face of an adhesive tape, the above method cannot copy the fingerprint clearly. Instead of the above method, a method in which 2-cyanoacrylate is vaporized and converted to white polymers with moisture on a fingerprint so as to detect the fingerprint has been used as a method for developing a fingerprint residue more clearly.

The detection of fingerprint using 2-cyanoacrylate is usually carried out by means of allowing a vapor of 2-cyanoacrylate (monomer) to adhere to a fingerprint, and there have been various reports on details thereof, including a method in which a gel formulation is used as disclosed in Patent Document 1, a method in which 2-cyanoacrylate (monomer) is dropped to powder so as to volatize as disclosed in Patent Document 2, a method in which 2-cyanoacrylate (monomer) is sprayed as disclosed in Patent Document 3, a method in which 2-cyanoacrylate (monomer) is impregnated into woven or non-woven fabric as disclosed in Patent Document 4, and so on.

However, since 2-cyanoacrylate polymer attached to fingerprint is white, it can hardly detect the fingerprint on whitish specimens such as shopping bags and aluminum foils, and is disadvantageous in that it requires an advanced technique for taking a picture such as photographing with oblique rays.

To address the above problems, detection with high sensitivity has been made possible by allowing a fingerprint ridge obtained from 2-cyanoacrylate polymer to contain a fluorescent colorant so as to emit fluorescence in accordance with a method in which a mixture of 2-cyanoacrylate and a fluorescent colorant is sprayed as disclosed in Patent Document 5, a method in which 2-cyanoacrylate is allowed to adhere to a fingerprint, and then soaked in a solution of a fluorescent colorant so as to be developed for detection as disclosed in Patent Document 6, and the like.

However, these wet methods using organic solvents cannot avoid deterioration of specimens by the organic solvents when specimens made of plastics or the like are used. Also, organic solvents are problematic in terms of flammability and toxicity.

To address the above problem, a method has been reported, which is a dry method in which vapors of 2-cyanoacrylate (monomer) and a sublimation dye are simultaneously used as disclosed in Patent Document 7.

However, when a fluorescent colorant is used in combination with 2-cyanoacrylate as in Patent Documents 5 and 7, a basic fluorescent colorant cannot be used due to solidification of 2-cyanoacrylate, and thus a disadvantage arises in that kinds of fluorescent colorants which can stably be used are largely limited. In addition, it is not preferable that 2-cyanoacrylate is used in combination with fluorescent colorants from the viewpoints of storage stability and handling at the scene.

Moreover, all the above-described methods for detecting a fingerprint using 2-cyanoacrylate have a problem such that 2-cyanoacrylate polymer is difficult to be wiped from the specimen in order to restore it after fingerprint has been detected, and thus inferior in restorability.

Patent Document 1: JP-A-S60-502088
Patent Document 2: JP-A-S60-222033
Patent Document 3: JP-A-S61-288836
Patent Document 4: JP-A-S62-47343
Patent Document 5: JP-A-S63-161939
Patent Document 6: JP-A-H02-268744
Patent Document 7: JP-A-H11-9575

DISCLOSURE OF THE INVENTION

Problems to be Solved by the Invention

An object of the present invention is to provide specific polymer and composition easy to handle at the scene of fingerprint detection, instead of conventionally used 2-cyanoacyrlate (monomer). Also, it intends to provide a method which can detect a fingerprint with high sensitivity regardless of color or condition of specimens, and is good in restorability of specimens. Meanwhile, restorability in the present invention means ease of wiping to remove fingerprint ridges from specimens.

Means for Solving the Problem

As a result of diligent researches in view of the above mentioned problems, the present inventors have found that when a polymer obtained by reacting a 2-cyanoacrylate with a specific fluorescent colorant or composition comprising a 2-cyanoacrylate polymer and a specific fluorescent colorant is used, fingerprint detection can be carried out with ease of handling at the scene and high sensitivity. Further, they have found an unexpected fact that when the polymer or composition is used for detection of fingerprint, restorability of specimens is improved, and have finally completed the present invention.

That is, the present invention is structured as follows:

1) A polymer for detecting a fingerprint, which is obtained by polymerizing a 2-cyanoacrylate by use of a polymerization initiator that comprises a fluorescent colorant represented by the following formula (1):

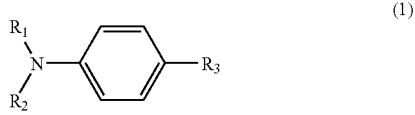

(1)

wherein $R_1$ and $R_2$ each represent an alkyl group with 1-3 carbon atoms, and $R_3$ represents an aldehyde group or an alkyl or alkenyl group that has 1-6 carbon atoms and has an aldehyde group at a terminal thereof.

2) A polymer for detecting a fingerprint, according to the above item 1), wherein the fluorescent colorant is selected from p-dimethylaminobenzaldehyde, p-diethylaminobenzaldehyde, p-dipropylaminobenzaldehyde, p-dimethylaminocinnamaldehyde, p-diethylaminocinnamaldehyde, p-dipropylaminocinnamaldehyde, 5-(4-dimethylamino-phenyl)-penta-2,4-dienal, 5-(4-diethylamino-phenyl)-penta-2,4-dienal and 5-(4-dipropylamino-phenyl)-penta-2,4-dienal.

3) A polymer for detecting a fingerprint, according to the above item 2), wherein the fluorescent colorant is p-dimethylaminobenzaldehyde or p-dimethylaminocinnamaldehyde.

4) A polymer for detecting a fingerprint, according to the above item 2), wherein the 2-cyanoacrylate is selected from methyl-2-cyanoacrylate, ethyl-2-cyanoacrylate, propyl-2-cyanoacrylate and isopropyl-2-cyanoacrylate.

5) A method of producing a polymer for detecting a fingerprint, which comprises polymerizing a 2-cyanoacrylate in a presence of a fluorescent colorant represented by the formula (1).

6) A method of producing a polymer for detecting a fingerprint, according to the above item 5), which comprises a first step of mixing a solution containing a fluorescent colorant with a solution containing a 2-cyanoacrylate, a second step of polymerizing the 2-cyanoacrylate in the solution, and a third step of distilling off a solvent after polymerization of the 2-cyanoacrylate.

7) A method of producing a polymer for detecting a fingerprint, according to the above item 6), wherein the solvent is acetone.

8) A method of producing a polymer for detecting a fingerprint, according to the above item 6), which further comprises a fourth step of crushing the polymer for detecting a fingerprint.

9) A method of producing a polymer for detecting a fingerprint, according to the above item 6), wherein the fluorescent colorant is selected from p-dimethylaminobenzaldehyde, p-diethylaminobenzaldehyde, p-dipropylaminobenzaldehyde, p-dimethylaminocinnamaldehyde, p-diethylaminocinnamaldehyde, p-dipropylaminocinnamaldehyde, 5-(4-dimethylamino-phenyl)-penta-2,4-dienal, 5-(4-diethylamino-phenyl)-penta-2,4-dienal and 5-(4-dipropylamino-phenyl)-penta-2,4-dienal.

10) A method of producing a polymer for detecting a fingerprint, according to the above item 9), wherein the above fluorescent colorant is p-dimethylaminobenzaldehyde or p-dimethylaminocinnamaldehyde.

11) A method of producing a polymer for detecting a fingerprint, according to the above item 6), wherein the 2-cyanoacrylate is selected from methyl-2-cyanoacrylate, ethyl-2-cyanoacrylate, propyl-2-cyanoacrylate and isopropyl-2-cyanoacrylate.

12) A composition for detecting a fingerprint, which comprises a 2-cyanoacrylate polymer polymerized by use of a polymerization initiator other than one represented by the formula (1), and a fluorescent colorant represented by the formula (1).

13) A composition for detecting a fingerprint, according to the above item 12), wherein the polymerization initiator other than one represented by the formula (1) is water, methanol or an amine.

14) A method for detecting a fingerprint, which comprises vaporizing a polymer for detecting a fingerprint defined in any one of the above items 1)-4) by hearting so as to allow it to adhere to a fingerprint, and obtaining an image of the fingerprint ridge as a fluorescence image.

15) A method for detecting a fingerprint, which comprises vaporizing a polymer for detecting a fingerprint obtained by the method of producing a polymer for detecting a fingerprint according to any one of the above items 5)-11) by heating so as to allow it to adhere to a fingerprint, and obtaining an image of the fingerprint ridge as a fluorescence image.

16) A method for detecting a fingerprint, which comprises vaporizing a composition for detecting a fingerprint according to the above items 12) or 13) by heating so as to allow the composition to adhere to a fingerprint, and obtaining an image of the fingerprint ridge as a fluorescence image.

Usually, the depolymerization temperature at which the 2-cyanoacrylate polymer initiates to depolymerize by heating is around 200° C., and when a high temperature is used near a specimen, the specimen may be damaged. However, it has been found that when the polymerization is conducted by use of the above fluorescent colorant as an initiator, the depolymerization temperature is lowered thanks to the initiating group located at terminals thereof, so that the gas can be generated at a relatively low temperature (around 130-160° C.). Also, it has been found that an addition of the fluorescent colorant to a previously-polymerized 2-cyanoacrylate followed by heating causes depolymerization concurrently with partial polymerization being induced by the fluorescent colorant as an initiator, and thus the same effect of lowering the depolymerization temperature is obtained.

Effect of the Invention

The polymer and composition for detecting a fingerprint according to the present invention make it possible to quickly detect a fingerprint with high sensitivity regardless of color or condition of the specimen. In addition, the polymer and the composition provide good restorability for the specimen when the specimen is made of a metal such as aluminum, and thus are easy to handle.

BEST MODE FOR CARRYING OUT THE INVENTION

Examples of the 2-cyanoacrylate used in the present invention include methyl-2-cyanoacrylate, ethyl-2-cyanoacrylate, propyl-2-cyanoacrylate, isopropyl-2-cyanoacrylate, butyl-2-cyanoacrylate, isobutyl-2-cyanoacrylate, amyl-2-cyanoacrylate, hexyl-2-cyanoacrylate, cyclohexyl-2-cyanoacrylate, octyl-2-cyanoacrylate, 2-ethylhexyl-2-cyanoacrylate, allyl-2-cyanoacrylate, benzyl-2-cyanoacrylate, methoxyethyl-2-cyanoacrylate, ethoxyethyl-2-cyanoacrylate, methoxypropyl-2-cyanoacrylate and tetrahydrofurfuryl-2-cyanoacrylate, and these 2-cyanoacrylates can be used alone or in combination of two or more. Of these, methyl-2-cyanoacrylate, ethyl-2-cyanoacrylate, propyl-2-cyanoacrylate and isopropyl-2- cyanoacrylate are preferable from the viewpoint of adhesiveness to fingerprint of depolymerized 2-cyanoacrylate monomers.

Examples of the fluorescent colorant of the following formula (1) used in the present invention include p-dimethylaminobenzaldehyde, p-diethylaminobenzaldehyde, p-dipropylaminobenzaldehyde, p-dimethylaminocinnamaldehyde, p-diethylaminocinnamaldehyde, p-dipropylaminocinnamaldehyde, 5-(4-dimethylamino-phenyl)-penta-2,4-dienal, 5-(4-diethylamino-phenyl)-penta-2,4-dienal and 5-(4-dipropylamino-phenyl)-penta-2,4-dienal. These fluorescent colorants can be used alone or in combination of two or more. Of these, p-dimethylaminobenzaldehyde and p-dimethylaminocinnamaldehyde are preferable from the viewpoint of association with depolymerized 2-cyanoacrylate monomers.

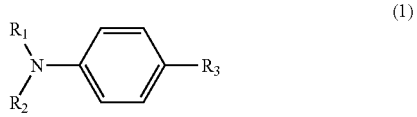

(1)

wherein $R_1$ and $R_2$ each represent an alkyl group with 1-3 carbon atoms, and $R_3$ represents an aldehyde group or an alkyl or alkenyl group that has 1-6 carbon atoms and has an aldehyde group at a terminal thereof.

Referring to the amount of the fluorescent colorant to be used, it can be added or mixed in an arbitrary amount relative to 2-cyanoacrylate.

The polymer for detecting a fingerprint according to the present invention can be obtained as follows. To a solution of a fluorescent colorant for the present invention in acetone, a solution of 2-cyanoacrylate (monomer) in acetone is added, and the mixture is polymerized in acetone, followed by removal of acetone (hereinafter, the resultant polymer is referred to as reacted polymer). It is preferable to crush the reacted polymer into powder form in order to reduce unevenness.

In addition, the composition comprising a 2-cyanoacrylate polymer resulting from polymerization with a polymerization initiator other than one represented by the formula (1) according to the present invention, and a specific fluorescent colorant (hereinafter referred to as powder mixture) can be obtained as follows. A 2-cyanoacrylate (monomer) is previously polymerized by use of water, methanol, an amine or the like as an initiator, and is subjected to reprecipitation with methanol or the like to obtain a purified polymer followed by supplementing and mixing a fluorescent colorant for the present invention therewith.

EXAMPLE

Hereinafter, the present invention will be described in more detail by way of Examples and Comparative Examples, however, the present invention is not limited to these examples.

Examples 1-12, Comparative Examples 1-4

0.2 g of a reacted polymer or powder mixture obtained using ethyl-2-cyanoacrylate (ARONALPHA 201 manufactured by TOAGOSEI CO., LTD.) and a fluorescent colorant shown in Table 1 was vaporized by heating (150-240° C.×20 minutes) in a glass vessel (280×280×300 mm), and was allowed to adhere to a latent fingerprint on an aluminum foil attached to the wall of the vessel, in order to detect a fluorescent fingerprint and evaluate restorability. Also, thermogravimetric analysis (TGA) was performed, in order to determine a temperature at which vaporization was initiated according to tangent method using the TGA chart.

(Method for Producing Reacted Polymers)

To a 5 mass % solution in acetone of a fluorescent colorant shown in Table 1, a 10 mass % solution in acetone of ethyl-2-cyanoacrylate was added in a ratio shown in Table 1. The mixture was allowed to react at 25° C. for 24 hours, and then acetone was removed. The reacted polymer thus obtained was used for the test.

(Method for Producing Powder Mixtures)

To 10 g of ethyl-2-cyanoacrylate, 3 ml of methanol containing 1 mass % of water was added, and the mixture was left for not less than one day at 25° C. so as to effect polymerization. The resulting polymer was dissolved in 300 ml of acetone, and then the acetone solution was subjected to reprecipitation with 200 ml of methanol three times, followed by vacuum filtration and drying under reduced pressure to yield ethyl-2-cyanoacrylate polymer powder. The resulting ethyl-2-cyanoacrylate polymer powder and a fluorescent colorant shown in Table 1 were mixed in a ratio shown in Table 1, and used for the test.

(Method for Detecting a Fluorescent Fingerprint)

A fingerprint detected by using a polymer or mixture resulting from a fluorescent colorant other than dimethylbenzaldehyde colorants was irradiated with an ultraviolet to blue (blue LED, 475 mm) light, and the resulting fluorescent fingerprint image was observed through a filter cutting the irradiated light. A fingerprint detected by using a polymer or mixture resulting from dimethylbenzaldehyde colorants was irradiated with an ultraviolet (UV lamp, 365 nm) light, and the resulting fluorescent fingerprint image was observed through a filter cutting the irradiated light. The observed fluorescent fingerprint was pictured using a digital or film camera.

The level of fluorescent fingerprint detection was evaluated as follows.

◯: Fluorescent fingerprint ridge can be observed continuously and clearly.

x: Fluorescent fingerprint ridge is not observed or hard to observe.

(Method for Evaluating Restorability)

Fingerprint ridge adhering onto the aluminum foil was rubbed with a cotton swab five times, to observe removal of the fingerprint ridge.

The level of restoration was evaluated as follows.

◯: Fingerprint ridge can be removed completely or mostly.

:Fingerprint ridge can be removed a little.

x: No fingerprint ridge can be removed

Comparative Example 5

0.2 g of the ethyl-2-cyanoacrylate polymer powder prepared by the above mentioned method was not mixed with any fluorescent colorant, and was used alone for the test and evaluation in the same manner as above.

Comparative Examples 6 and 7

0.2 g of a fluorescent colorant shown in Table 1 was used alone for the test and evaluation in the same manner as above.

TABLE 1

| | Fluorescent colorant | Specimen preparation method | Cyanoacrylate:fluorescent colorant (mass ratio) | Vaporization initiating temperature (°C.) | Level of fluorescent fingerprint detection | Restorability (aluminum) |
|---|---|---|---|---|---|---|
| Example 1 | p-dimethylaminocinnamaldehyde | Reacted polymer | 1:1 | 138 | ○ | ○ |
| Example 2 | p-dimethylaminocinnamaldehyde | Reacted polymer | 2:1 | 144 | ○ | ○ |
| Example 3 | p-dimethylaminocinnamaldehyde | Reacted polymer | 4:1 | 153 | ○ | ○ |
| Example 4 | p-dimethylaminobenzaldehyde | Reacted polymer | 1:1 | 144 | ○ | ○ |
| Example 5 | p-dimethylaminobenzaldehyde | Reacted polymer | 2:1 | 152 | ○ | ○ |
| Example 6 | p-dimethylaminobenzaldehyde | Reacted polymer | 4:1 | 159 | ○ | ○ |
| Example 7 | p-dimethylaminocinnamaldehyde | Powder mixture | 1:1 | 128 | ○ | ○ |
| Example 8 | p-dimethylaminocinnamaldehyde | Powder mixture | 2:1 | 134 | ○ | ○ |
| Example 9 | p-dimethylaminocinnamaldehyde | Powder mixture | 4:1 | 142 | ○ | ○ |
| Example 10 | p-dimethylaminobenzaldehyde | Powder mixture | 1:1 | 130 | ○ | ○ |
| Example 11 | p-dimethylaminobenzaldehyde | Powder mixture | 2:1 | 136 | ○ | ○ |
| Example 12 | p-dimethylaminobenzaldehyde | Powder mixture | 4:1 | 144 | ○ | ○ |
| Comparative Example 1 | Rhodamine 6G | Reacted polymer | 1:1 | 143 | x | |
| Comparative Example 2 | 4-hydroxycoumarin | Reacted polymer | 1:1 | 166 | x | |
| Comparative Example 3 | Rhodamine 6G | Powder mixture | 1:1 | 154 | x | |
| Comparative Example 4 | 4-hydroxycoumarin | Powder mixture | 1:1 | 201 | x | |
| Comparative Example 5 | — | — | 10:0 | 203 | x | x |
| Comparative Example 6 | p-dimethylaminocinnamaldehyde | — | 0:10 | 180 | x | ○ |
| Comparative Example 7 | p-dimethylaminobenzaldehyde | — | 0:10 | 170 | x | ○ |

As it is clear from Table 1, when a reacted polymer obtained by reacting a 2-cyanoacrylate with a specific fluorescent colorant was used (Examples 1-6), or when a powder mixture of a 2-cyanoacrylate polymer and a specific fluorescent colorant was used (Examples 7-12) according to the present invention, the fluorescent fingerprint was clearly detected. Also, restorability of specimens was good. Further, comparing with the case where the above compounds were singly used (Comparative Examples 5-7), the vaporization initiating temperature was lowered so that the heat load to the specimen was suppressed. In contrast, when a conventional fluorescent colorant different from the fluorescent colorant according to the present invention was used (Comparative Examples 1-4), the vapor of the fluorescent colorant was not well associated with depolymerized 2-cyanoacrylate monomers so that they were not sufficiently placed together on the fingerprint ridge, and thus fluorescence was not clearly detected as in Comparative Examples. Also, when a 2-cyanoacrylate polymer is used alone (Comparative Example 5), restorability was not obtained.

Although the present invention was described above in detail referring to specific embodiments, it is apparent for those skilled in the art that various changes or modifications can be applied without departing from the spirit and scope of the present invention.

The present application is based on a Japanese patent application (Application No. 2006-274958) filed Oct. 6, 2006, the content of which is incorporated herein by reference.

Industrial Applicability

The polymer and composition for detecting a fingerprint and the method for detecting a fingerprint using these make it possible to clearly detect fluorescence even on whitish specimens such as shopping bags and aluminum foils which have conventionally been difficult for the detection. In addition, since the present invention is a dry method in which vaporization can be carried out at a relatively low temperature, it also keeps the damage of the specimen as low as possible. Further, restorability of the specimen is good when it is a metallic specimen such as of aluminum. Thus, it has been ensured that latent fingerprint can be detected from a wide range of specimens that have not conventionally been used.

Figure 1:
FIG. 1 is a photograph showing the result of fluorescent fingerprint detection. The upper half thereof shows Comparative Example 5, and the lower half thereof shows Example 4.
Figure 2:
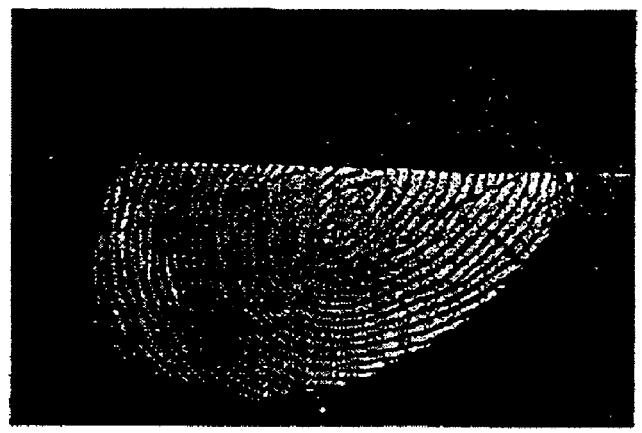
FIG. 2 is a photograph showing the result of fluorescent fingerprint detection. The upper half thereof shows Comparative Example 5, and the lower half thereof shows Example 7.
Figure 3:
FIG. 3 is a photograph showing the result of restorability test. The upper half thereof shows Comparative Example 5, and the lower half thereof shows Example 8, in a state that wiping was partly carried out.

The invention claimed is:

1. A composition for detecting a fingerprint, which comprises a 2-cyanoacrylate polymer polymerized by use of a polymerization initiator other than one represented by formula (1), and a fluorescent colorant represented by the formula (1):

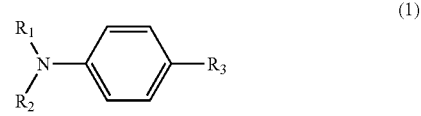

(1)

wherein $R_1$ and $R_2$ each represents an alkyl group with 1-3 carbon atoms, and $R_3$ represents an aldehyde group or an alkyl or alkenyl group that has 1-6 carbon atoms and has an aldehyde group at a terminal thereof, whereby when detecting said fingerprint, the polymer is depolymerized.

2. A composition for detecting a fingerprint according to claim 1, wherein the polymerization initiator other than one represented by the formula (1) is water, methanol or an amine.

* * * * *